United States Patent [19]
Holtz et al.

[11] Patent Number: 5,934,012
[45] Date of Patent: *Aug. 10, 1999

[54] PROCESS FOR PRODUCTION OF MUSHROOM INOCULUM

[75] Inventors: Richard Barry Holtz; Michael J. McCulloch, both of Vacaville, Calif.

[73] Assignee: HPS Biotechnologies, Inc., Vacaville, Calif.

[ * ] Notice: This patent issued on a continued prosecution application filed under 37 CFR 1.53(d), and is subject to the twenty year patent term provisions of 35 U.S.C. 154(a)(2).

[21] Appl. No.: 08/344,243

[22] Filed: Nov. 23, 1994

[51] Int. Cl.$^6$ ...................................................... A01G 1/04
[52] U.S. Cl. ........................... 47/1.1; 435/410; 435/254.1
[58] Field of Search ............................. 435/240.4, 254.1, 435/410; 47/1.1

[56] References Cited

U.S. PATENT DOCUMENTS

| | | |
|---|---|---|
| 2,850,841 | 9/1958 | Szuecs . |
| 2,928,210 | 3/1960 | Cirillo . |
| 3,286,399 | 11/1966 | Laniece . |
| 4,083,144 | 4/1978 | Fuzisawa et al. ........................... 47/1.1 |
| 4,420,319 | 12/1983 | Holtz . |
| 4,810,504 | 3/1989 | Schindler . |
| 5,123,203 | 6/1992 | Hiromoto .................................. 47/1.1 |

FOREIGN PATENT DOCUMENTS

| | | |
|---|---|---|
| 2070715 | 8/1992 | Canada . |
| 2215464 | 8/1974 | France . |
| 2603048 | 2/1988 | France . |
| 2436793 | 2/1976 | Germany . |

OTHER PUBLICATIONS

Patent Abstracts of Japan, vol. 018, No. 086 (C–1165), Feb. 14, 1994.
JP,A,05 292917 (Kureha Chem Ind Co Ltd), Nov. 9, 1993.

*Primary Examiner*—Leon B. Lankford, Jr.
*Attorney, Agent, or Firm*—Albert P. Halluin; John A. Bendrick; Howrey & Simon

[57] ABSTRACT

This invention relates to a submerged fermentation process for producing high biomass levels of mushrooms mycelia in liquid media suitable for semi-continuous or continuous mushroom spawn production. The process provides a sterile, log phase inoculum for a solid substrate that, when based on biomass, exceeds normal inoculation levels by several thousand fold mycelia substrate production. The liquid inoculum so produced can be aseptically transferred to bulk sterilizer to inoculate a sterilizer grain or sawdust substrate for commercial mushroom production. The liquid inoculum may also be inoculated directly onto the mushroom compost. This invention further relates to microcapsules used to enhance the fermentation process and the equipment used to conduct such process.

33 Claims, 7 Drawing Sheets

# PROCESS FOR PRODUCTION OF MUSHROOM INOCULUM

TECHNICAL FIELD OF THE INVENTION

The present invention relates to a submerged fermentation process for producing high biomass levels of mushroom mycelia in liquid media and liquid media useful in such process and suitable for semi-continuous or continuous mushroom spawn production. The subject invention also relates to a sterile, log-phase mushroom inoculum and a fermentor useful for producing mushroom mycelia in a submerged culture.

BACKGROUND OF THE INVENTION

Processes for making inoculum cultures used to produce edible mushrooms on a suitably prepared substrate are well known. Processes suitable for the efficient large-scale production of mycelia inoculum, however, are notably absent from the art.

Early production methods involved the use of a solid culture medium such as tobacco, grain and manure which have been shown to support the growth of vegetative mycelia. These methods require an undesireably extended period of time (i.e., 30 to 60 days) for the mycelium to attain a suitable developmental stage, and are labor-intensive, requiring several manual transfers of aseptic materials as production is scaled up. The manual transfers have traditionally used very low ratios of inoculum to new substrate to maximize yield of product. In addition, efforts to produce commercial amounts of mycelia inoculum using a solid culture medium process occasionally resulted in adverse selection pressure of a particular mushroom strain.

A submerged fermentation process using liquid media reduces the time required to produce mushroom mycelia inoculum. Some techniques involving the use of liquid ("submerged") culture techniques are taught in the prior art. For example, U.S. Pat. No. 3,286,399 discloses the production of mushroom spawn after sowing with mycelium or spores in a submerged culture that consists of carbohydrate- and nitrogen-containing nutrients. U.S. Pat. No. 5,077,201 discloses the production of blue indigo pigment from a strain of morel mushroom by submerged fermentation in a nutrient medium containing a carbon and a nitrogen substrate. U.S. Pat. No. 4,977,902 discloses the production of Pleurotus sp. and Volvaria sp. in a liquid media adapted for plastic packaging.

These submerged culture techniques, however, are not suitable for producing large amounts of mycelia suitable for commercial mushroom production. Submerged culture basidiomycete mycelia by conventional fermentation techniques forms very large, clumped colonies that are dense balls of mycelia. This cultural problem limits the amount of biomass that can be produced and forms the same selection pressures on the biomass that cold be expected in solid state culture. Large colony formation limits the points of inoculation that could be obtained from the fermentation broth. Accordingly, a submerged fermentation process that can use liquid media for the generation of larger amounts of mycelia suitable for commercial mushroom production is needed.

The suitability of submerged culture techniques to produce liquid mushroom mycelia inoculum for commercial use also depends on the efficiency of submerged mycelial growth. Growth efficiency depends largely on the content of medium nutrients and the growth conditions of the fermentation process. For example, Agaricus sp. does not grow well on starch and corn gluten in the absence of sufficient amounts of soluble protein and other nutrients, such as those suggested by U.S. Pat. No. 3,286,399. European Pat. No. 284,421 discloses the cultivation of filamentous fungi by inoculation onto a substrate comprising a variety of nutrients ranging from carbohydrates, nitrogens, lipids, nucleotides, sterols, vitamins and inorganic compounds to plant and bacterial extracts. This medium is sufficient to "sustain" the growth of the fungi, but does not "enhance" the growth of mycelia. U.S. Pat. No. 4,512,103 describes mushroom growth on undefined liquid nutrients produced by thermophilic digestion of biodegradable organic materials.

Prior art references provide only limited descriptions of processes in which mushroom growth is enhanced by the selection of a specified nutrient media. U.S. Pat. No. 4,370,159 discloses a 30% increase in growth and yield of edible mushroom by use of a nutrient particle comprising a matrix of denatured protein containing droplets of fat and active protein. This medium is useful for "mature mycelial" in commercial compost which is near the cropping stage. It is not suitable for non-mature mycelia and spores. U.S. Pat. No. 4,420,319 discloses nutritional enhancement additives comprising an agglomerate of activator and slow-release nutrient particles. Although this material reduces the time required for mushroom spawn to reach fruition and further retards premature aging of the cells, it appears to be suitable primarily for mushroom spawn which has already been inoculated onto seed grain. U.S. Pat. No. 4,818,268 discloses an osmoprotectant for enhancing mushroom growth which comprises carrier particles having water-soluble phosphoglyceride material attached. This osmoprotectant is used for enhancing and prolonging mushroom growth and for extending cropping by protecting the later flushes against the effects of increased osmotic stress. None of these prior art references, however, are directed to a medium for enhancing the growth of mycelia suitable for inoculation at a commercial mushroom production level. Identification of a liquid medium capable of enhancing the growth of mushroom mycelia to a commercially acceptable level is needed.

In addition to the identification of nutrients for use in liquid media to enhance the growth of mycelial inoculum, a commercially feasible process must be capable also of continuous or semi-continuous preparation of inoculated substrate in an automated, aseptic system. To achieve this commercial goal, a medium is needed that is capable of producing large quantities of log-phase inocula at a uniform growth stage. At present, only low yields of Agaricus mycelia from submerged culture growth have been achieved. Accordingly, a liquid medium suitable for the production of large amounts of log-phase mycelial inoculum at a uniform growth stage is needed.

The prior art further is silent with respect to a continuous or semi-continuous method for inoculating sterile substrates useful in the commercial production of mushrooms. Commercially feasible mushroom spawn must be capable of producing a cost-effective, aseptic fermentation of submerged culture mycelia that can be coupled with a continuous or semi-continuous inoculation of sterile substrates. These substrates must be compatible with current methods of inoculation at commercial mushroom farms which include the use of grains such as rye or millet as a substrate. These grains are convenient to admix into the compost. Additionally, the process should provide for the direct inoculation of the compost with the liquid culture through conventional spawning equipment fitted with suitable liquid discharge equipment.

SUMMARY OF THE INVENTION

The present invention relates to a submerged fermentation process capable of producing high biomass levels of mycelia in a liquid medium suitable for semi-continuous or continuous mushroom spawn production. The process comprises inoculating a liquid fermentation medium with inoculum and fermenting the inoculated media at a suitable temperature and under a gas containing an appropriate concentration of $CO_2$. The liquid media is designed to enhance the stable and continuous growth of the inoculum. Constant agitation during fermentation is provided by an impeller or by airlift in the fermentor. The inoculated medium is further sheared mechanically according to a fermentation-stirring schedule. The growth of mycelia, the pH and the $Co_2$ concentration of the fermentation mixture are monitored by suitable methods and the mycelia are harvested when their growth reaches an appropriate concentration.

The high levels of biomass of the mycelia may be used for the inoculation of a solid substrate suitable for commercial mushroom growing. The mycelia so produced, when based on biomass, exceed inoculation levels typically used by those persons skilled in the art by several thousand-fold in various mushroom mycelia, including Agaricus, Lentinus (Shiitake), Morchella (Morel), Pleurotus (oyster mushroom), *Flammulina velutipes* and *Volvariella volvacea* substrate production. This higher inoculation ratio provides more biomass and more points of inoculum. The growth of the mycelia is very uniform and is completed in about 10 days as compared to the typical 21 or more days of growth required in traditional spawn production systems. This represents a significant time savings to the grower with consequential cost savings.

The present invention also relates to the use of microcapsules in liquid media to enhance the growth of mushroom mycelia. These microcapsules comprise a lipid substrate which comprises between about 50% and 80% of the dry weight of the microcapsule, a surfactant which comprises between about 1% and 5% by weight of the lipid substrate, a dairy or vegetable protein which comprises between about 20% and 50% of the dry weight of the microcapsule and a Group II metal salt which comprises between about 0.1% and 0.5% of the dry weight of the microcapsule.

The present invention is further directed to a fermentor useful in producing high biomass levels of mycelia in a liquid medium suitable for continuous or semi-continuous mushroom spawn production.

BRIEF DESCRIPTION OF THE FIGURES

The invention will be better understood by reference to the attached drawings of which.

DETAILED DESCRIPTION OF THE INVENTION

Figure 1:
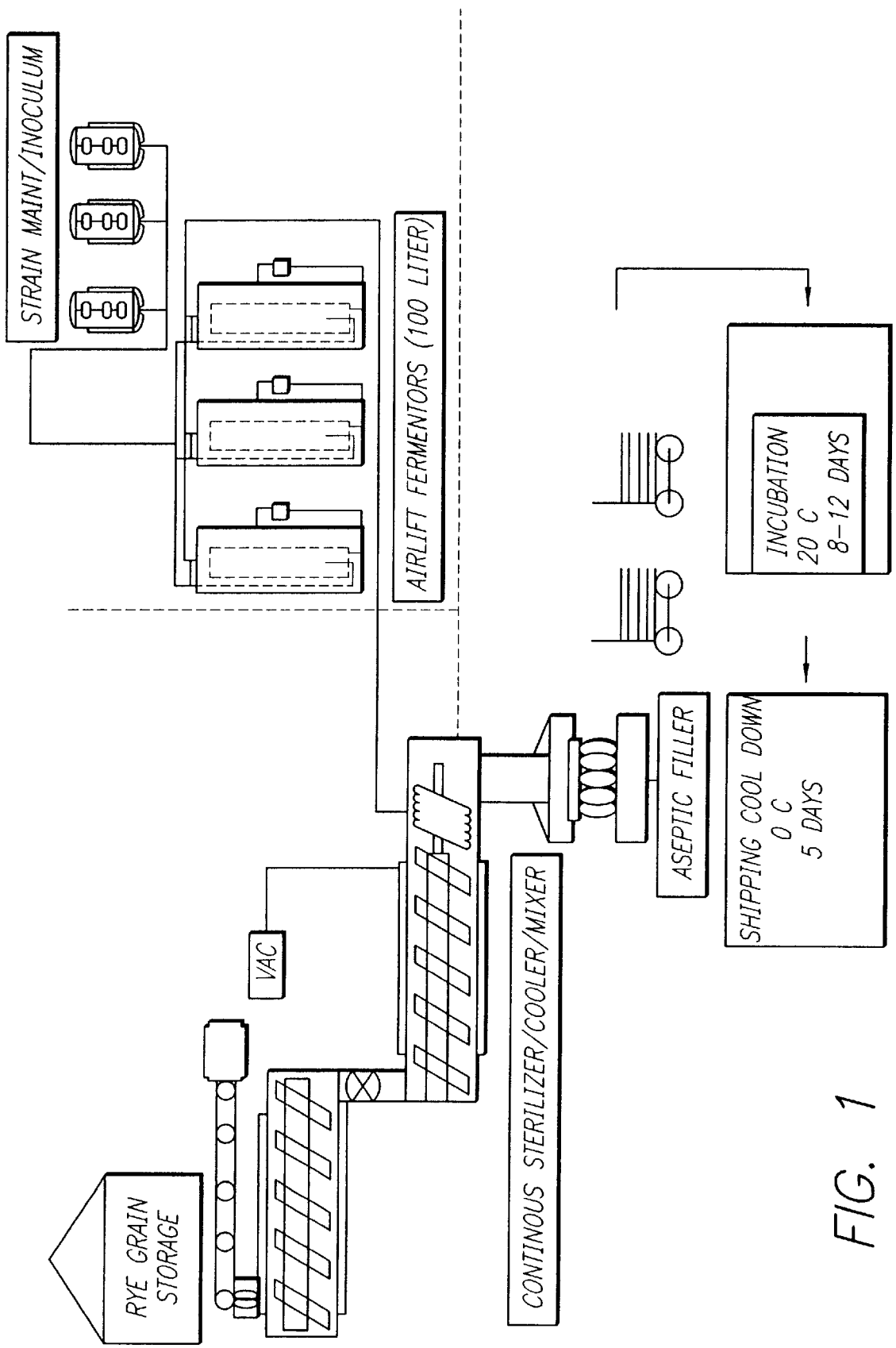
FIG. 1 depicts an aseptic substrate preparation system according to the invention with the continuous auger type sterilizer system.

The present invention relates to a fermentation process for producing high biomass levels of mushroom mycelia in liquid media, a liquid medium for producing such mycelia and a fermentor useful for producing mushroom mycelia in a submerged culture.

The fermentation process of the present invention comprises growing mushroom mycelia in a liquid fermentation medium (nutrient broth), where the fermentation temperature is between about 20° C. and 30° C., the air flow is between about 0.1 and 0.3 volume air/volume vessel per minute, the pH is between about 6.5 and 7.6 and the carbon dioxide is maintained at between about 2500 to 5000 ppm. The contents of the fermentation (fermentation broth) should be constantly agitated at a tip speed of between about 5 and 10 inches per second. In addition, the fermentation broth should be periodically subjected to shearing forces, for example, by agitating the fermentation at a speed of between about 25 and 100 inches per second of blade tip speed for periods of between about 1 and 3 minutes. In order to achieve maximum growth, it is preferred to shear the colonies every other day, thus keeping colony size small and uniform, thereby producing more points of inoculation in the final substrate.

The present invention also provides a convenient method for culture maintenance. Unlike traditional spawn processes, the liquid system of the invention provides much more stability in the maintenance of cultures. Typical grain spawn systems require that the inoculum be scaled-up in several steps in successively larger grain jars. However, there are a number of environmental and metabolic variables that can impose subtle selection pressure on the spawn such as temperature, $CO_2$ and nutrient composition. Being a heterokaryon, it is likely that this pressure can result in quality assurance problems and eventually the change of the phenotype due to the selection of a specific genetic strain. The nutrient composition provided by the present invention is particularly suitable for use in a fermentor system which is capable of providing a controlled, homogeneous environment that does not impose selection pressure on the mycelia.

The instant fermentation process provides the further benefit of producing compounds responsible for specific mushroom flavors. For example, preparing mushroom mycelial inoculum according to the above-described submerged fermentation process yields compounds responsible for the flavor of mushrooms. For example, use of the process to prepare Agaricus, Lentinus (Shiitake) or Morchella sp. (Morel) inoculum yields oct-1-ene-3-ol and oct-1-ene-3-one. Similarly, lentinan and other polysulfides are made by producing Lentinus (Shiitake) and 1-octanone is produced during the process for making Agaricus and *Morchella mycelial inoculum.*

The liquid medium of the invention comprises microcapsules which consist essentially of lipid substrate and an appropriate amount of lecithin or its equivalent. Suitable lipid substrate used in the present liquid medium comprises a polyunsaturated vegetable oil, including but not limited to, safflower, soybean, canola, corn and cottonseed. Microencapsulation allows the delivery of higher amounts of lipid substrate to submerged culture growth while maintaining uniformity of the nutrient in suspension.

These microcapsules comprise a lipid substrate which comprises between about 50 and 80% of the dry weight of the microcapsule, a surfactant which comprises between about 1% and 5% by weight of the lipid substrate, a dairy or vegetable protein which comprises between about 20% and 50%, most preferably 26% of the dry weight of the microcapsule and a Group II metal salt which comprises between about 0.1% and 0.5%, most preferably 0.2%, of the dry weight of the microcapsule.

The microcapsules are preferably formed by homogenizing in an aqueous solution wherein the microcapsules comprise between about 0.5% and 1.5% by dry weight of the combined microcapsule-nutrient media.

The surfactant is preferably either a phospholipid or a galactolipid, most preferably choline phosphatides, ethanolamine phosphatides, mixtures of choline and ethanolamine phosphatides, and choline and ethanolamine phosphatides containing hydroxylated fatty acids. Microencapsulation of the lipid substrate and surfactant is achieved by homogenizing the lipid substrate and surfactant in an aqueous solution containing a soluble dairy or vegetable protein such as whey protein concentrate, caseinates or soy protein concentrates, a Group II metal salt and an organic acid salt. Ridgtek H-20® Whey protein concentrate (e.g., Ridgtek H-20®), calcium chloride and sodium acetate are the preferred protein source, Group II metal salt and organic acid salt, respectively.

Nutrient media for submerged cultures of Agaricus microcapsules are prepared by blending soya bean, cottonseed, or safflower oil with 3% lecithin (Centrolene A® lecithin, Central Soya) and adding it to 1 g of whey protein concentrate, such as Ridgtek H-20, 100 ml water with 1 g of calcium chloride and 0.7 g of sodium acetate. These materials should account for about 0.22% of the dry weight of ingredients of the total medium. These ingredients are then homogenized in a high-shear, high-speed mixer (Polytron type) to form microcapsules and sterilized in an autoclave. 250 grams of potato infusion is prepared by boiling 250 g potatoes in 0.9 liter of water for 15 minutes and filtering through cheesecloth. 20 g of autolyzed yeast extract and 10 g of dextrose (or 35 g of 40 DE corn syrup or 15 g honey) is added to the infusion. This material is then sterilized and combined with the sterile microcapsules. The total volume for the above formulation is approximately 1 liter.

The microcapsule-containing media of the present invention has been found to significantly enhance mycelial growth (dry weight) in a shake flask culture. For example, potato-dextrose-yeast (PDY) extract-based broth typically supports between about 0.75 and 1.2 g/l of mycelial growth (dry weight) in a shake flask culture. By contrast, the same PDY media where the microcapsules of the present invention have been added supports yields in excess of 7.6 g/l of mycelial growth (dry weight) in shake flask.

The present invention also relates to fermentors for the production of mycelia in a submerged culture. Mycelia inoculum may be prepared in a production fermentor. The inoculation of a 100-liter production fermentor is accomplished directly from a 1.5 liter culture maintenance fermentor (for example, an autoclavable Wheaton 1.5 liter Minijar® fermentor). The same fermentation protocol is maintained with the 1.5 liter fermentor as with the production stirred tank vessel. The Minijar fermentor is equipped with a specially built marine turbine having a diameter of 1.5 inches. The turbine has a square edge on the outer diameter. The rotor speed is maintained at about 100 rpm which is the lowest controllable limit for this system. This is equivalent to a rotor tip speed of about 7.85 in/sec.

Figure 6:
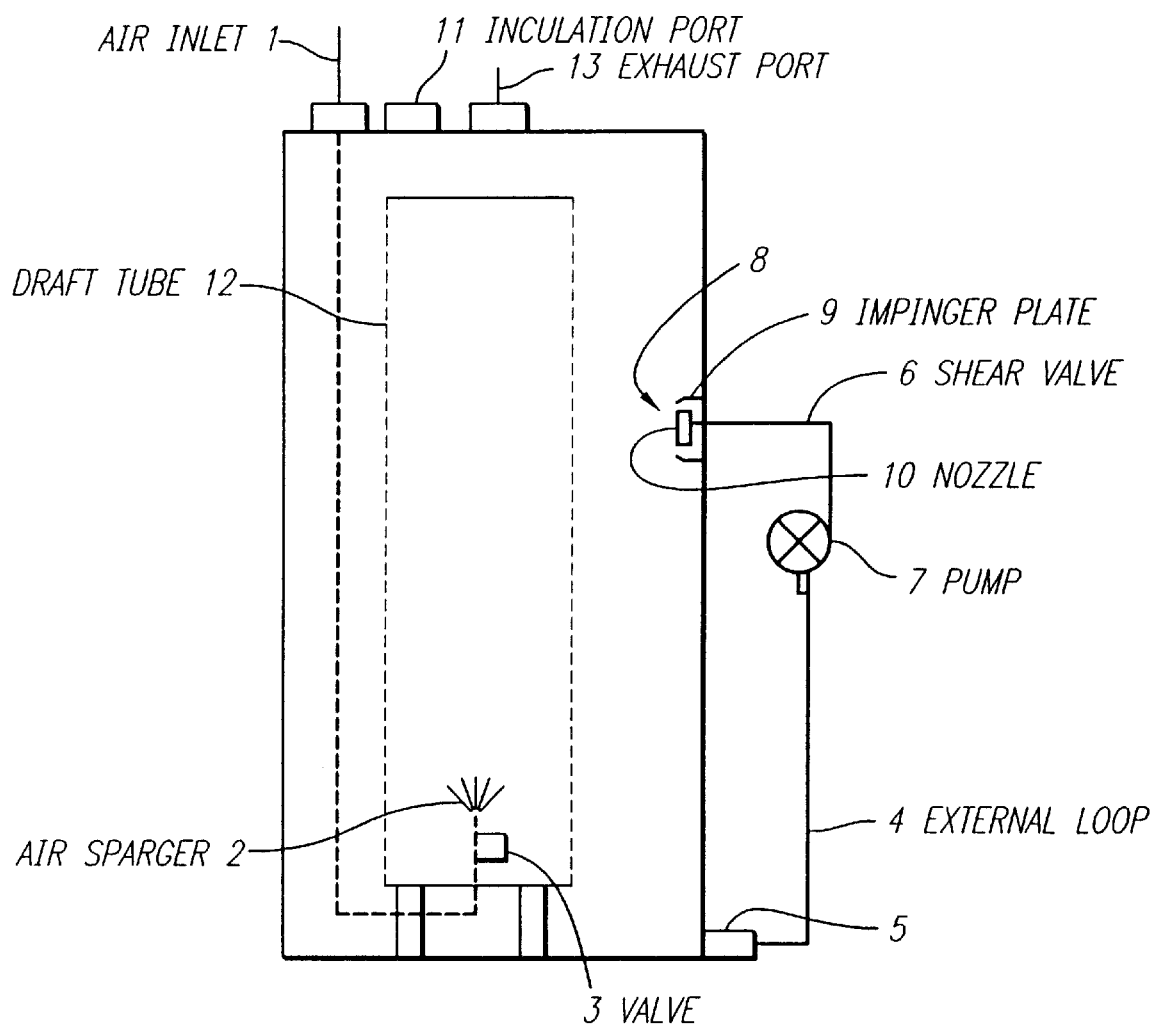
FIG. 6 depicts the diagram of the airlift 100-liter production fermentor.

A preferred embodiment of a fermentor used to produce mycelia in a submerged culture is an "airlift" type fermentor. The "airlift" fermentor was designed and constructed to provide a cost-effective, autoclavable bioreactor for mycelial growth. A typical airlift fermentor is depicted in FIG. 6. This design is scaleable to 100 liters which is the largest vessel that will fit conveniently in standard autoclaves. An autoclavable vessel is much less costly to build than a sterilizable-in-place (SIP) fermentor. Since there is very little metabolic heat of fermentation, a large heat exchange surface is not necessary. The fermentor vessel can be placed in a temperature-controlled room or in an incubator for temperature control during fermentation. Aeration and airlift is provided by an air delivery manifold in the incubator having sufficient size to contain multiple vessels or in the temperature-controlled room.

The airlift fermentor typically contains an air inlet connected to an air sparger. The air sparger contains a mixing valve which allows carbon dioxide and nitrogen gas to be mixed with compressed air to create a relatively high carbon dioxide atmosphere within the fermentor. The fermentor is preferably run at about 0.2 volume of inlet gas/volume of vessel/minute. The carbon dioxide is generally adjusted to between about 2500 and 5000 ppm, depending upon the strain of fungus being grown.

The fermentor also has an external loop of latex tubing connecting a port on the bottom of the vessel to a Tri-Clover® port on the side of the vessel. The latex tubing can be threaded through a peristaltic pump without detachment from the sterile vessel. The peristaltic pump can pump the suspended mycelia in a loop that contains a specialized shear valve consisting of an adjustable impinger plate in front of a stainless nozzle inside the vessel.

As it is preferred to shear the colonies of mycelia for maximum growth every other day in order to keep the colony size small and uniform, thus producing more points of inoculation in the final substrate, a fermentor must also provide a mechanism for such shearing. This device provides a portable, inexpensive way to accomplish the shear process without having a driven shaft and turbine in place. A driven shaft and turbine device on this vessel would add greatly to the cost, complexity, and risk of contamination.

Sterile grain substrate is prepared by a semi-continuous blend/sterilizer system or by a continuous, auger-type sterilizer. Once the culture has reached log-phase growth, the biomass is transferred to the sterile substrate produced by the continuous or semi-continuous grain sterilizer system.

The following examples are given to demonstrate the use of the process according to the present invention for large-scale mushroom production. They are only intended for illustrative purposes and are not meant to limit the invention described herein.

EXAMPLE 1—Use of Liquid Inoculum in Continuous Inoculation System Design for Commercial Spawn Production Fermentation A commercial system has been designed using the engineering data generated at the laboratory bench and at the pilot plant production scale. A schematic of the process is shown in FIG. 1. On the commercial scale, a "pre-blender" (1) blends solid substrate materials with water. Rye grain or millet and chalk are blended in the case of Agaricus spawn and hardwood sawdust and nutrients are blended in the case of Shiitake. The substrate is introduced into sterilizer screw (2) via rotary "star" valve (3) to maintain a high pressure environment in the sterilizer. The sterilizer screw (2) (See Table 2 for detailed procedures for sterilization) is a thermal screw-type reactor, including a hollow auger type screw that can be heated by steam. Residence time in the sterilizer is adjustable. A period of approximately 15 minutes is commonly used. The residence time can be closely controlled by adjusting the speed of the auger. The substrate is then transferred to cooling screw (4). A steam-ejection system with condensate control is used to precisely regulate the residual moisture of the substrate. Inoculum from a series of fermentors A, B and C is then pumped into the a secondary section of the cooling screw that has been modified for highest mixing capabilities. As the cooled substrate migrates to this section, the substrate and mycelial inoculum are thoroughly mixed. The mixture is then aseptically packaged using any of several well-known bagging systems (e.g., "Pouchmaster®"). The system is extremely efficient and non-labor intensive due to its high degree of automation. The hardware is readily selected from proven equipment in the biotechnology and food equipment industries.

Inoculation

Inoculation is accomplished by using a peristaltic pump to transfer inoculum from fermentors A, B and C to the mixing section of cooling screw (4). A latex rubber transfer line was autoclaved and attached using sterile technique to the corresponding steam-sterilizable ports on the fermentor and the sterilizer. In our tests, a Wheaton (Heidolf-type) Omnispense® pump was used to deliver inoculum at a rate of 240 ml/min. 1.6 liters of inoculum was used per batch. Two batches could be effectively produced in the system per day.

One liter of fermentation broth, containing approximately 6 g of *Agaricus mycelia,* is recommended for 500 lbs of finished spawn product. Agitators in the fermentors were run continuously at 8 rpm during the transfer of inoculation and for 5 minutes after completion of inoculation. The growth rates of the inoculum are accelerated due to the high level of actual biomass transferred to the substrate. The growth is extremely uniform due to the homogeneous mixing of the inoculum and substrate. The growth is further enhanced by the transfer of sophisticated micro-encapsulated nutrients that are transferred from the unused media onto the substrate.

TABLE 2

Sterilization protocol for grain was as follows:

Preheat sterilizer or fermentor jacket to 115° C. for 20 minutes.
Load all ingredients
Start agitator (8 rpm).
Open steam injection valve, adjust pressure to 18 psi.
Maintain a constant vent through the vent valve.
Maintain pressure for 18 minutes.
Stop introducing steam.
Open filtered vent valve, and start cooling water.
Reduce the temperature of the grain to <260° C. and proceed with inoculation.
90 lbs of fungicide-free rye grain (Guistos Vita Grain Co., South San Francisco, CA)
was added to the sterilizer with 258 lbs (30 gallons) of water and 2 lbs of $CaCO_3$.

Figure 2:
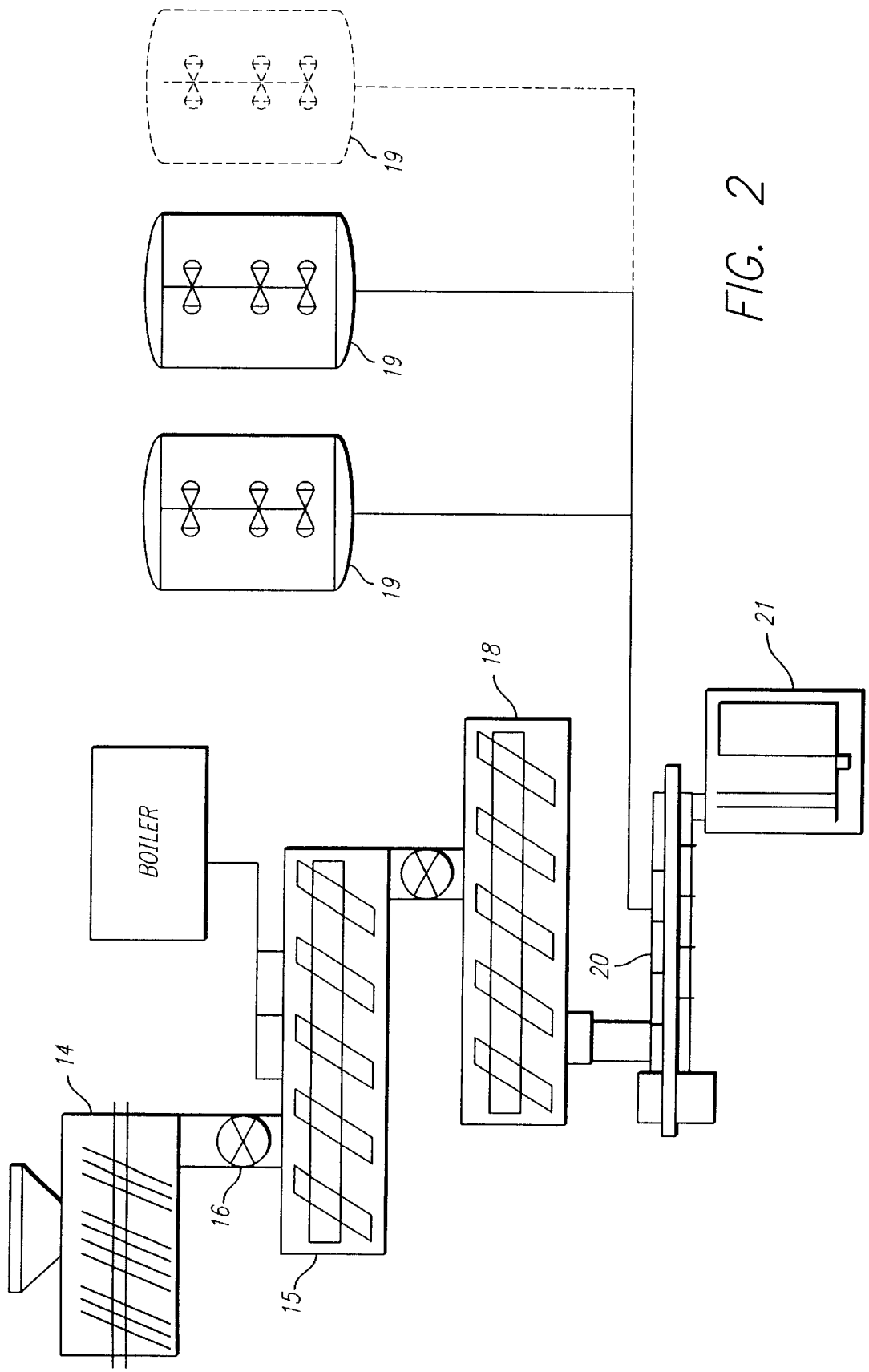
FIG. 2 depicts an aseptic substrate preparation system according to the invention with the semi-continuous blender/sterilizer system.
Figure 3:
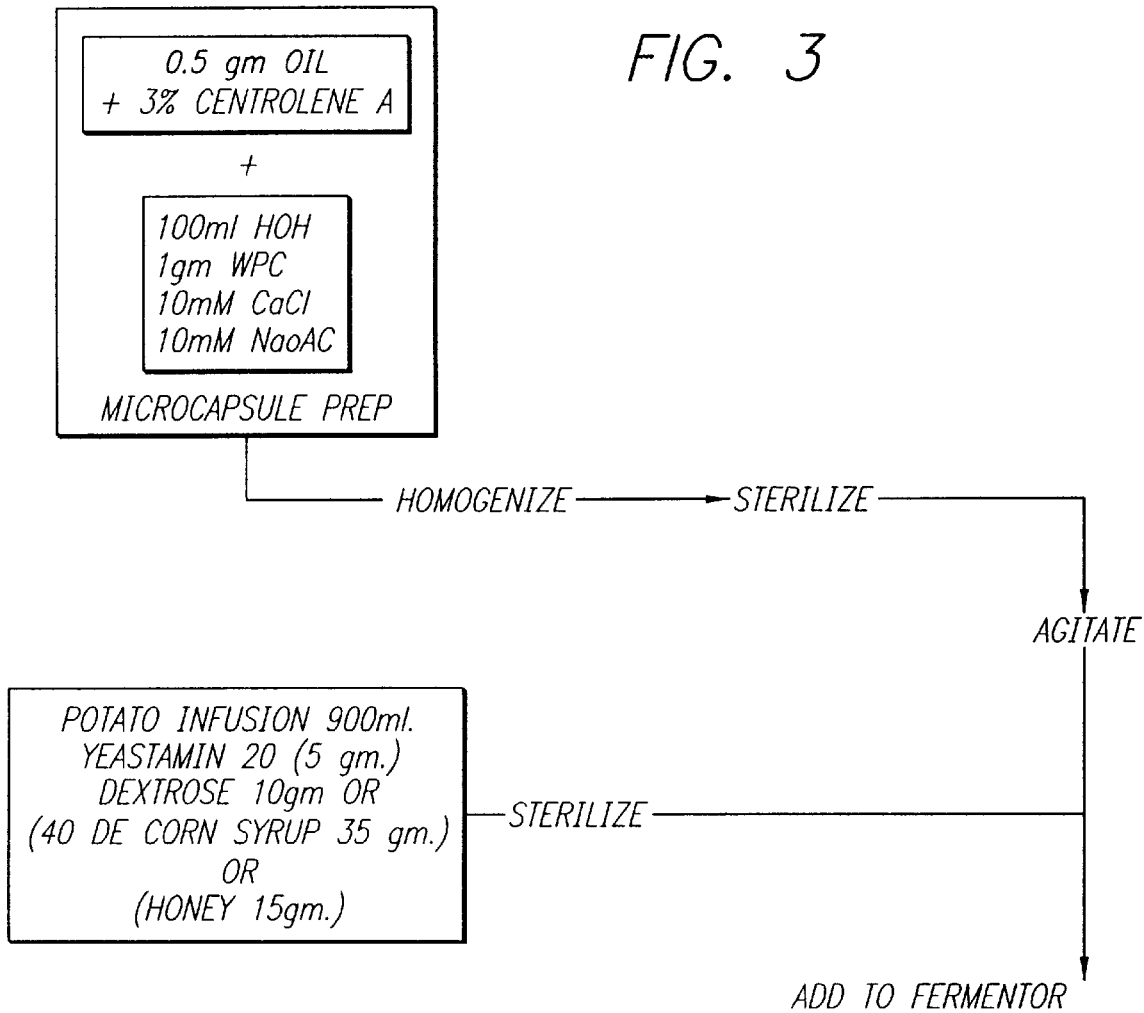
FIG. 3 depicts the steps used to prepare the liquid medium of the invention.
Figure 4:
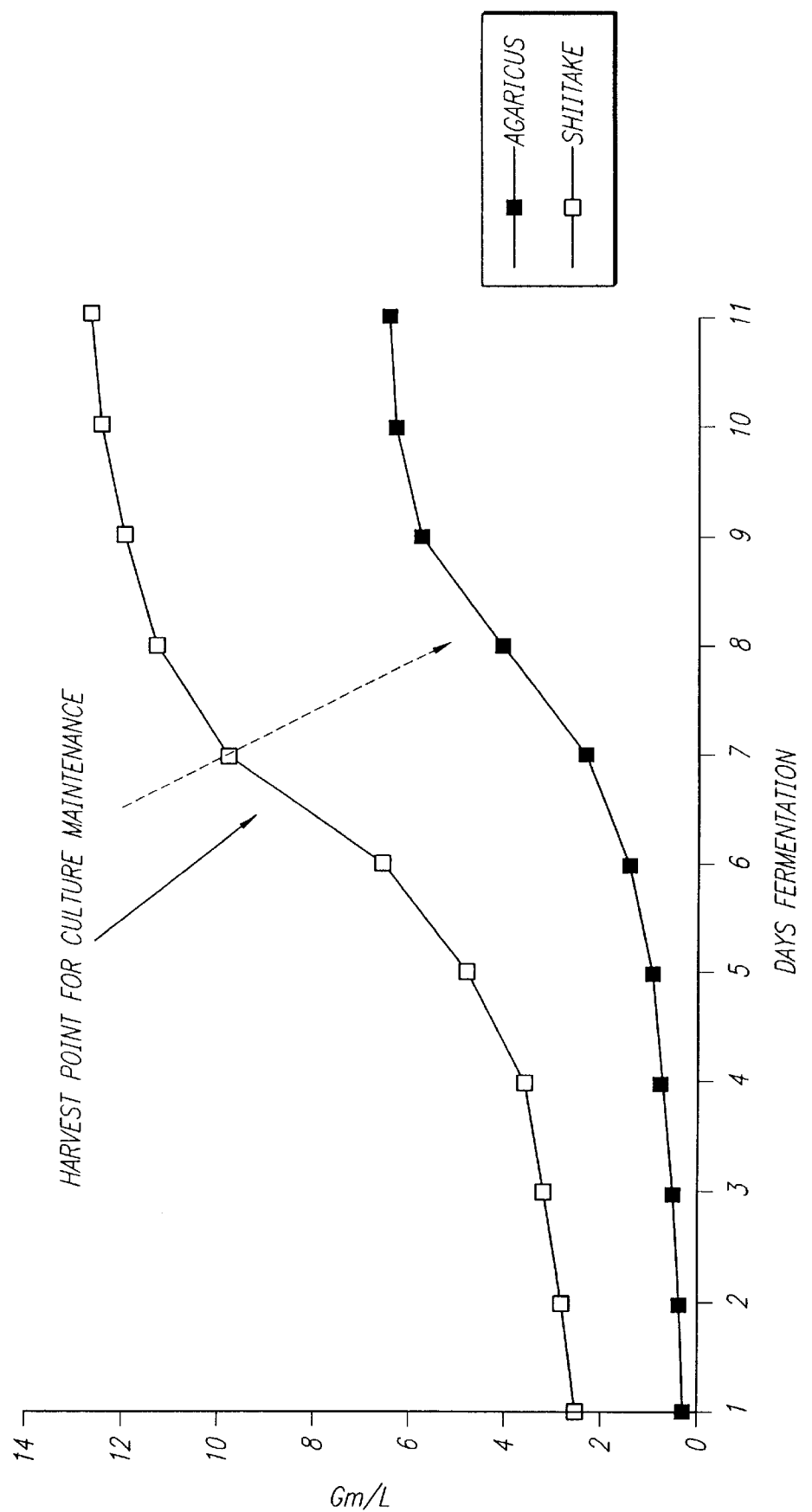
FIG. 4 depicts the harvest point for culture maintenance for both Agaricus and shiitake strains.

EXAMPLE 2—Use of Liquid Inoculum in a Semi-Continuous Inoculation System Design for Commercial Spawn Production FIG. 2 shows the flow diagram for a semi-continuous system of grain preparation that uses a plow-blender type sterilizer, such as a Littleford FKM-1200-D, that can sterilize and vacuum cool in the same vessel. After cooling, the sterile grain/chalk/water mixture is discharged into a surge hopper. Several blenders are used to supply enough sterile substrate to allow the next steps, inoculation and filling, to proceed continuously. The sterile substrate is blended with the inoculum from the fermentors in the ratios described in Example 1 using an aseptic scraped-surface mixer. The inoculated grain is then filled aseptically into pouches as described in Example 1.

EXAMPLE 3—Fermentation Pilot Plant Development for

Shiitake Strain

Fermentation was carried out as described above in Example 1. Fermentation temperatures were adjusted to accommodate different temperature optima for each strain. Some Shiitake strains can be grown successfully in warmer environments. One hot-weather strain tested required a 26° C. fermentation temperature. Inoculation rates were between about 1.6 liters and 3.6 liters of total fermentation broth per 1000 lbs of substrate.

(a) Substrate Preparation

A variety of substrate were used to develop successful Shiitake substrate for the submerged culture technique. A typical formulation was based on the quality of the hardwood sawdust available as the principal substrate. The preferred substrate is a sawdust between about 10 and 26 mesh (Standard US Sieve) and preferably consisting of oak or oak/alder mix. The moisture content is typically between about 30–45% but must be tested before each batch.

Based on dry weight the following proportions of materials are used for substrate: 79% sawdust, 10% millet, 10% wheat bran and 1% $CaCO_3$. The moisture of the sterile substrate should not exceed about 63% for most Shiitake strains.

(b) Packaging

Inoculated substrate was packaged continuously into sterile bags under a HEPA-filtered hood for Agaricus spawn preparation. Bags were heat-sealed for closure. 3.4 lbs of inoculated substrate were added per bag.

(c) Incubation

Bags were maintained at an internal temperature of 26° C. in a refrigerated incubator. The bags were incubated until fully colonized. The mycelia and substrate at this point form a firm block of biomass. Depending on the strain, this initial incubation takes between about 26 and 34 days. After this period the bags were transferred to mushroom growing rooms.

(d) Fruiting

To induce fruiting, the bag was opened and peeled back so that approximately 50% or greater of the biomass was exposed. The bag was then watered repeatedly over a three day period to saturate the sawdust log with water. The air temperature was reduced to about 180° C. At least about 6 hours of light was provided by fluorescent lighting per day to stimulate fruiting. The logs began to produce mushrooms at about between 45–50 days post-inoculation and can produce mushrooms for as long as approximately 120 days. The yield was typically between about 0.75 and 1.0 lbs of fresh weight per pound of dry weight of substrate.

EXAMPLE 4—Direct Inoculation of Mushroom Compost with Liquid inoculum.

Figure 7:
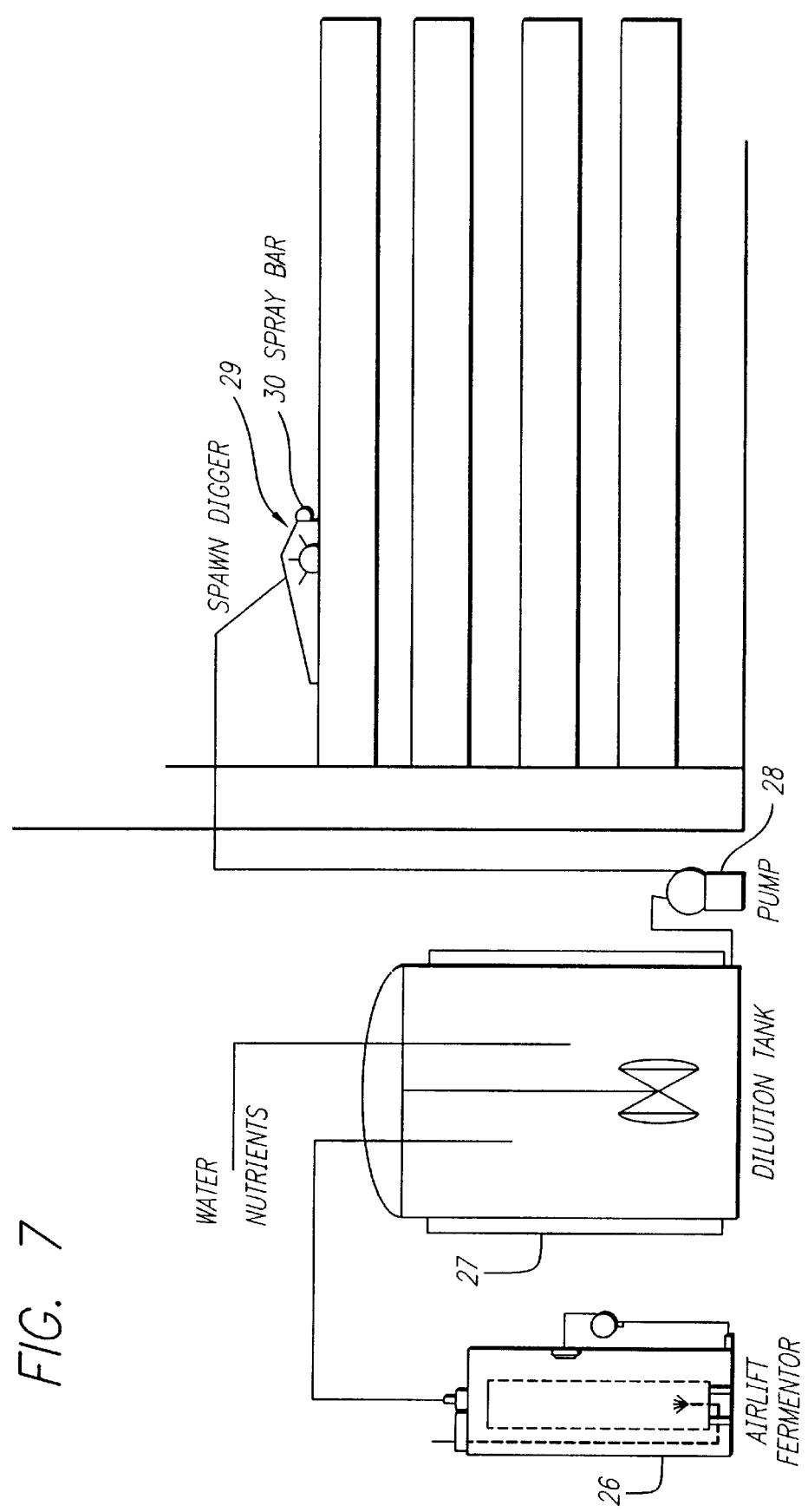
FIG. 7 depicts the direct inoculation of compost with liquid mycelia.

Liquid inoculum can be directly inoculated into mushroom compost prepared in the conventional manner (FIG. 7). The submerged culture can be transported to the mushroom farm using an insulated truck to maintain temperature and additionally equipped with a portable compressor to maintain aeration. In a commercial inoculation, 100 liters of submerged culture is diluted and mixed into between 800 and 1000 gallons of water containing approximately 500 grams of microcapsules prepared as described above in the DETAILED DESCRIPTION OF THE INVENTION. The diluted culture is then pumped to the spawning machine where it is dispensed through a spray bar as the machine is mixing the compost. This process is readily adaptable to all types of commercial cultural processes. A typical 8000 square foot commercial mushroom house requires approximately 2000 lbs of conventional grain spawn to thoroughly inoculate the compost. Tests were run using the equivalent of 100 liters of submerged culture for 8000 square feet of compost. The spawn run temperatures were typical of a normal grain spawn inoculated compost, however, visual appearance of abundant white mycelia did not appear until the 11th day due to the finer points of inoculation as compared to mycelial inoculum grown on grain. At the time of casing (14th day of the spawn run) the mycelial colonization looked identical to a grain spawn-inoculated control. Yields were comparable with no difference in quality. This method of delivery could greatly reduce the cost of raw materials and the cost of application of spawn to the mushroom house.

EXAMPLE 5—Spawn Fermentation Pilot Plant

Figure 5:
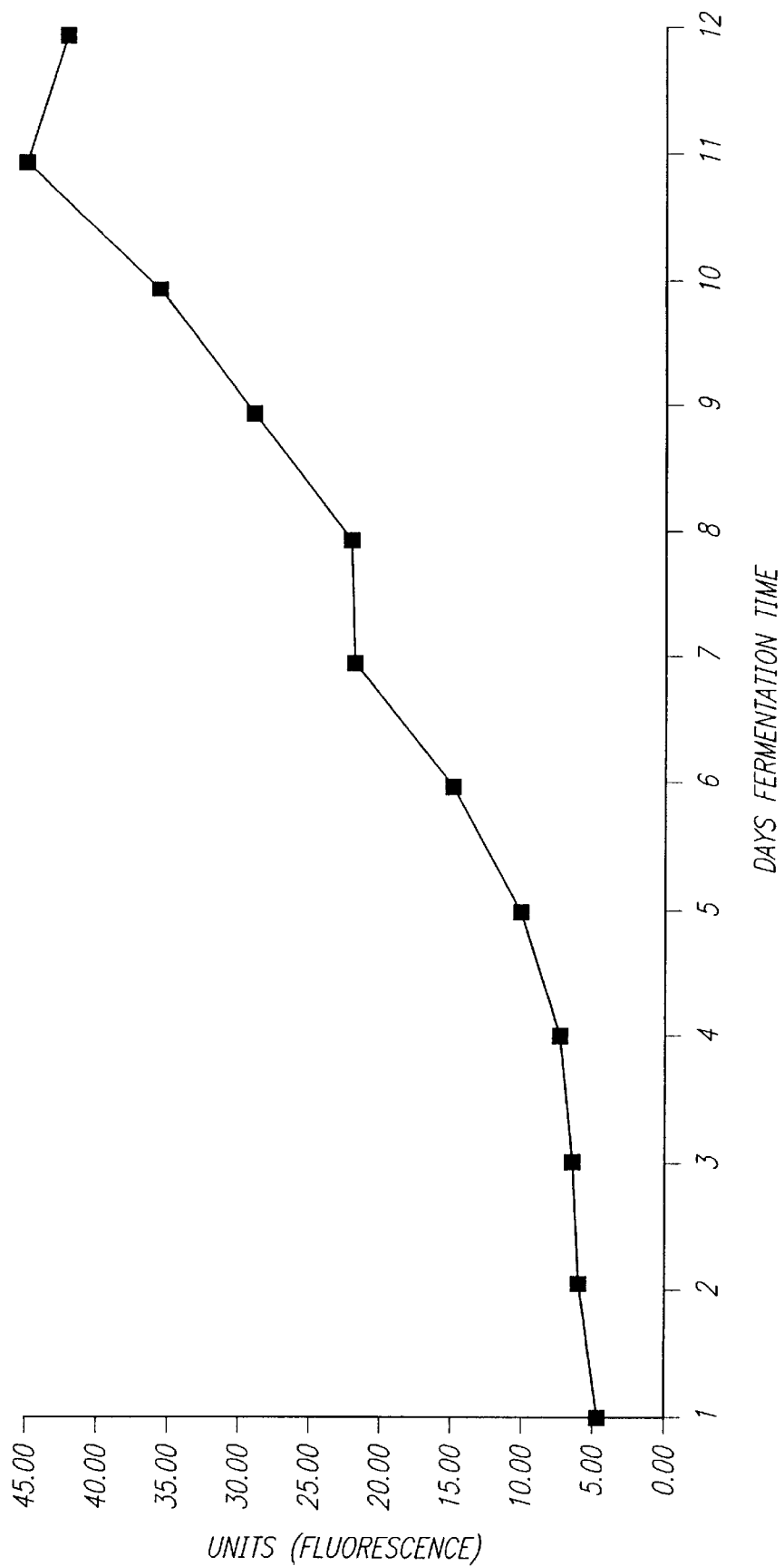
FIG. 5 depicts the rate of mycelia growth as expressed by fluorescence units for shiitake.

An important feature of the present invention is the establishment of a spawn fermentation pilot plant. By way of example and not a limitation, the following 30 liter fermentor was used to demonstrate the feasibility of mycelial fermentation (e.g. a Braun Biostat®). This fermentor was equipped with a draft tube and marine impellers. The aspect ratio of this vessel is 2.4/1. The working volume of the fermentor was 20 liters. The growth curves of Agaricus and Shiitake mycelia in this fermentor were monitored by fluorescent techniques as shown in FIG. 5. A preferred fermentation protocol is shown in Table 1.

TABLE 1

Fermentation Conditions for Schedule-
Stirred Tank 30-Liter Braun

Stirring Schedule

Day 1- Inoculation- 0.1 g biomass/l
Day 4- Shear (2 min @ 109 in/sec)
Day 6- Shear (2 min @ 109 in/sec)
Day 8- Shear (3 min @ 109 in/sec)
Day 11- Harvest
Standard Conditions Marine Impeller (32.7 in/sec)
Temperature- 22° C. (71.6° F.)
Air Flow 0.3 V/V approx. 9800 units
ppm $CO_2$ (Strain Dependent)
pH 7.6 to 6.5 (monitor only)
$DO_2$ (monitor only)

The rate of the mycelial development of Shiitake spawn in the fermentor is determined by a Fluoromeasure Probe (FIG. 5). The probe measures the fluorescence of NADH in the cells of the mycelium. The increase in fluorescence correlates well with the traditional measurement of the biomass by dry weight. This technology negates the necessity of multiple samplings to determine the various growth stages of the culture in the fermentor. Although this technique has been used to measure biomass in bacterial fermentations, to the inventors' knowledge, this has never before been used for fungal biomass determination.

EXAMPLE 6—Spawn Growth and Production Tests

A series of spawn strains were obtained from the culture collection at Ostrom's Mushroom Farm, Olympia, WA. Experiments were conducted with four types of spawn that represented 90% of the types of spawn being used in commercial culture. These strains were 0–681-Hybrid White Strain, 0–235-Off-White Strain, 0–681-Hybrid White Strain and 0–1001 Hybrid Off-White.

These strains were grown in supplemented and unsupplemented composts and were compared against the commercial strains cited above. Spawn run temperatures, yield of mushrooms/square foot, and grower evaluation were monitored. In all cases the experimental material performed equal to or better than the commercial material. At no time were any aberrant symptoms of spawn degeneration such as clefting, hard gill, stroma, and aerial hyphal development noted. The experimental material usually had a temperature profile slightly elevated from the commercial form. This indicates higher metabolic levels. The mycelia colonized the compost more rapidly and penetrated the casing layer more rapidly than typical commercial methods. This is demonstrated by the fact that in the experimental crops, extra casing material had to be added ("patched") due to the accelerated colonization of the spawn into the casing layer. This procedure allows the induction of fruiting in both the experimental and control crops at the same time. If the mycelia of all of the boxes in a growing room are not the same level in the casing when the room environment is changed to induce fruiting, the newly formed mushrooms will not all mature at the same time and cause difficulty evaluating the yield.

A typical commercial spawn run continues for 14 days before the casing material is applied. In most cases, a significant temperature surge is noted on the 6th or 7th day after spawning. A commercial crop, supplemented with delayed-release nutrients, spawned at the rate of 1 lb per 6 square feet of bed area and a compost dry weight of approximately seven pounds of dry weight per square foot can be expected to have a temperature differential between about 15° F. and 20° F. between air and compost due to thermogenic metabolism. This profile shows the typical commercial temperature curves and indicates a strong vegetative growth profile. Yields at the research facility are typically between about 6.5 and 8.0 lbs/ft$^2$ depending on the experimental conditions and supplements used.

The aforementioned examples illustrate the various features of the present invention but are not intended to limit the scope of the invention as set forth in the claims. Numerous modifications and variations are possible in light of the teachings of the instant invention and are intended to be within the scope of the appended claims.

What is claimed is:

1. A process for producing mushroom mycelia comprising:
   (a) preparing a liquid medium, wherein said liquid medium comprises microcapsules containing polyunsaturated liquid oils comprising between about 50% to 80% of the microcapsule;
   (b) inoculating said liquid medium with an inoculum;
   (c) fermenting said inoculated medium under appropriate conditions;
   (d) inoculating said medium onto sterile solid substrate suitable for mushroom growth; and
   (e) fermenting said solid substrate under appropriate conditions.

2. The process according to claim 1, wherein the mushroom mycelia are selected from the group consisting of *Agaricus bisporus, Lentinus edodes,* Morchella sp., Pleurotus sp., *Flammulina velutipes,* and *Volvariella volvacea.*

3. The process of claim 1, wherein said polyunsaturated oil of step (a) is a plant seed oil selected from the group consisting of: soya bean oil, cottonseed oil and safflower oil.

4. The process according to claim 1, wherein said microcapsule of step (a) further comprises:
   (a) a surfactant which comprises between about 1% and 5% by weight of the polyunsaturated oil lipid substrate;
   (b) a dairy or vegetable protein which comprises between about 20% and 50% of the dry weight of the microcapsule;
   (c) water in an amount of between about 80% and 92%, and
   (d) a Group II metal salt which comprises between about 0–1% and 0.5% of the dry weight of the microcapsule.

5. The process according to claim 4, wherein the microcapsule further comprises:
   (a) a salt of an organic acid between about 0.05% to 0.1%;
   (b) potato infusion resultant from the use of about 250 grams of peeled potatoes per liter of water, (c) autolyzed yeast extract (20 grams/liter medium); and
   (d) a source of carbohydrate.

6. The process according to claim 4, wherein the surfactant of the microcapsule is selected from the group consisting of choline phosphatides, ethanolamine phosphatides, mixtures of choline and ethanolamine phosphatides, and choline and ethanolamine phosphatides containing hydroxylated fatty acids.

7. The process according to claim 4, wherein the dairy or vegetable protein of said microcapsule is selected from the group consisting of: whey protein concentrates, caseinates and soy protein concentrates.

8. The process according to claim 4, wherein the Group II metal salt of said microcapsule is calcium chloride.

9. The process according to claim 5, wherein the salt of said organic acid is sodium acetate.

10. The process according to claim 5, wherein the source of said carbohydrate is selected from the group consisting of: dextrose having a concentration of about 10 g/l 40 DE corn syrup having a concentration of about 35 g/l, and honey having a concentration of about 15 g/l.

11. The process according to claim 1, wherein the fermentation conditions of step (c) comprise:
   (a) growing said culture in an airlift fermentor which comprises:
      (i). a vessel with an aspect ratio of between about 2.5.1 (h×d) and 4:1 (h×d);
      (ii). a draft tube positioned within the vessel, wherein the diameter of the draft tube is between about 0.3 to 0.5 times the diameter of the vessel;
      (iii). an external pumping loop;
      (iv). an outlet port and inlet port on the vessel;
      (v). an external pumping loop connecting the outlet and inlet ports;
      (vi). a shear valve connected to the inlet port which shears the liquid pumped through the shear valve; and
      (vii). a gas inlet sparger for sparging gas into the vessel;
   (b) agitating a fermentation mixture of step (b) constantly with an airflow from the draft tube;
   (c) shearing the fermentation mixture of step (c) with the shear valve of the airlift fermentor,
   (d) monitoring the growth of mycelia in the fermentation mixture and the dissolved oxygen by suitable methods.

12. The process of according to claim 11, wherein the vessel has capacity of between about 50 and 200 liters.

13. The process according to claim 11, wherein the fermentation broth is pumped through the external loop at a rate of between about 10 and 50 liters/min and contacted with a shear valve.

14. The process according to claim 11, wherein the fermentor is inoculated by a culture containing between about 2 to 5 grams biomass/liter.

15. The process according to claim 11, wherein the culture is maintained for a period of 8 to 11 days or until a density of biomass of 6 g/l is achieved.

16. The process according to claim 11, wherein the fermentation broth is pumped on alternating days during fermentation for a period of between about 2 to 20 minutes through an external loop at a rate of between about 10 and 50 liters/min and contacted with a shear valve.

17. The process according to claim 11, wherein the sterile fermentation broth is aseptically mixed with sterile grain.

18. The process according to claim 11, wherein the grain is sterilized in a continuous thermal screw-auger sterilizer and vacuum-cooled in a continuous thermal screw-auger sterilizer.

19. The process according to claim 11, wherein the grain is sterilized by heating to about 121° C. at a steam pressure of at least 15 psi for a period of between about 15 to 30 minutes.

20. The process according to claim 11, wherein the grain is slowly agitated during heating and vacuum-cooled before being inoculated from the fermentor.

21. The process according to claim 11, wherein the grain is sterilized and vacuum-cooled in a plow-blender sterilizer.

22. The process according to claim 11, wherein the sterile grain is aseptically admixed with the fermentation broth in a scraped-surface mixer.

23. The process according to claim 11, wherein the admixed grain and fermentation broth are aseptically packaged in a sterile plastic bag containing a suitable porous barrier strip to allow the emission of air without contamination from airborne microorganisms.

24. The process according to claim 11, wherein the aseptically packaged, admixed grain and fermentation broth are added to the compost for purposes of inoculation.

25. The process according to claim 11, wherein the fermentation broth is added directly to compost for purposes of inoculation.

26. The process according to claim 1, wherein the fermentation conditions of step (c) comprise:
   (a) growing said culture at a temperature of between about 20° C. to about 30° C. and with an air flow of between about 0.1 to about 0.3 volume air/volume vessel/min;
   (b) agitating the fermentation mixture of step (b) constantly by means of a mechanical device at an appropriate tip speed of between about 5.0 to about 10.0 inches/sec;
   (c) shearing the the inoculated medium of step (c) by a mechanical device;
   (d) maintaining the pH of said mixture at between about 6.5 to about 7.6; and
   (e) monitoring the growth of mycelia in the inoculated medium and the dissolved oxygen by suitable methods.

27. The process according to claim 26, wherein the vessel has capacity of between about 30 and 30,000 liters.

28. The process according to claim 26, wherein the density of the inoculated medium is between about 2 grams to 15 grams of biomass/liter of liquid medium.

29. The process according to claim 26, wherein said fermentation stirring schedule comprises:

(a) inoculating a culture of mushrrom at day 1;

(b) shearing the fermentation mixture for about 2 minutes at about 100 inches/second at day 4;

(c) repeating the same shearing at day 6; and (d) shearing the fermentation mixture for about 3 minutes at about 100 inches/second at day 8.

30. The process according to claim 26, wherein the fermentation mixture is sheared by stirring said mixture at a speed of between about 25.0 to about 100.0 inches/sec for about 1 to 3 minutes at predetermined intervals, said predetermined intervals being ranging from between about 24 to 48 hours, dependent on the mushroom strain used.

31. The process according to claim 11 or claim 26, wherein the growth of mycelia is monitored by measuring the fluorescence of NADH in the cells of said mycelia.

32. The process according to claim 11 or claim 26, wherein the mycelia are harvested at about eleven days after inoculation.

33. The process according to claim 31, wherein the mycelia are harvested when the fluorescence is about 45 units.

* * * * *

UNITED STATES PATENT AND TRADEMARK OFFICE
CERTIFICATE OF CORRECTION

PATENT NO. : 5,934,012

DATED : Aug. 10, 1999

INVENTOR(S): Richard Barry Holtz; Michael J. McCulloch, both of Vacaville, Calif.

It is certified that error appears in the above-identified patent and that said Letters Patent is hereby corrected as shown below:

Column 11, line 48..(a)(i) reference to "between about 2.5.1" SHOULD READ AS "between about 2.5:1"

Signed and Sealed this

Twenty-eighth Day of March, 2000

Attest:

Q. TODD DICKINSON

*Attesting Officer*  *Commissioner of Patents and Trademarks*